United States Patent
Wood et al.

(10) Patent No.: US 10,286,050 B2
(45) Date of Patent: May 14, 2019

(54) MULTI-EPITOPE TARP PEPTIDE VACCINE AND USES THEREOF

(71) Applicant: The United States of America, as represented by the Secretary, Department of Health and Human Services, Washington, DC (US)

(72) Inventors: Lauren V. Wood, Bethesda, MD (US); Jay A. Berzofsky, Bethesda, MD (US); Brenda D. Roberson, Frederick, MD (US); Masaki Terabe, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 168 days.

(21) Appl. No.: 15/102,996

(22) PCT Filed: Dec. 12, 2014

(86) PCT No.: PCT/US2014/070144
§ 371 (c)(1),
(2) Date: Jun. 9, 2016

(87) PCT Pub. No.: WO2015/089469
PCT Pub. Date: Jun. 18, 2015

(65) Prior Publication Data
US 2016/0310585 A1    Oct. 27, 2016

Related U.S. Application Data

(60) Provisional application No. 61/915,948, filed on Dec. 13, 2013.

(51) Int. Cl.
*A61K 39/00* (2006.01)
*A61K 9/19* (2006.01)

(52) U.S. Cl.
CPC ............ *A61K 39/0011* (2013.01); *A61K 9/19* (2013.01); *A61K 2039/5154* (2013.01); *A61K 2039/572* (2013.01); *A61K 2039/575* (2013.01); *A61K 2039/70* (2013.01)

(58) Field of Classification Search
None
See application file for complete search history.

(56) References Cited

U.S. PATENT DOCUMENTS

2005/0249742 A1* 11/2005 Ruprecht ............... A61K 38/10
424/185.1
2008/0008724 A1  1/2008 Aagaard et al.

FOREIGN PATENT DOCUMENTS

| JP | 2009-541373 | 11/2009 | | |
|---|---|---|---|---|
| WO | WO 01/04309 | 1/2001 | | |
| WO | WO-0116163 A2 * | 3/2001 | ............ | C07K 14/005 |
| WO | WO 2005/000889 | 1/2005 | | |

OTHER PUBLICATIONS

Kobayashi et al. (Clip Cancer Res. May 15, 2005;11(10):3869-78). (Year: 2005).*
Ferrante, Front Immunol. Oct. 1, 2013;4:308, pp. 1-6 (Year: 2013).*
Lin et al., BMC Bioinformatics 2008, 9(Suppl 12):S22, pp. 1-10 (Year: 2008).*
Essand et al., "High expression of a specific T-cell receptor γ transcript in epithelial cells of the prostate," *Proc Natl Acad Sci USA* 96:9287-9292, 1999.
Kenter et al., "Phase I Immunotherapeutic Trial with Long Peptides Spanning the E6 and E7 Sequences of High-Risk Human Papillomavirus 16 in End-Stage Cervical Cancer Patients Shows Low Toxicity and Robust Immunogenicity," *Clin. Cancer Res.*, vol. 14:169-177, 2008.
Mirshahidi et al., "Overlapping Synthetic Peptides Encoding TPD52 as Breast Cancer Vaccine in Mice: Prolonged Survival," *Vaccine*, vol. 27:1825-1833, 2009.
Oh et al., "Human CTLs to Wild-Type and Enhanced Epitopes of a Novel Prostate and Breast Tumor-Associated Protein, TARP, Lyse Human Breast Cancer Cells," *Cancer Res.*, vol. 64:2610-2618, 2004.
Welters et al., "Induction of Tumor-Specific CD4+ and CD8+ T-Cell Immunity in Cervical Cancer Patients by a Human Papillomavirus Type 16 E6 and E7 Long Peptides Vaccine," *Clin. Cancer Res.*, vol. 14:178-187, 2008.
Wolfgang et al., "T-Cell Receptor γ Chain Alternate Reading Frame Protein (TARP) Expression in Prostate Cancer Cells Leads to an Increased Growth Rate and Induction of Caveolins and Amphiregulin," *Cancer Res* 61(22):8122-8126, 2001.

(Continued)

*Primary Examiner* — Zachary S Skelding
(74) *Attorney, Agent, or Firm* — Klarquist Sparkman, LLP

(57) ABSTRACT

Immunogenic T cell receptor γ alternate reading frame protein (TARP) peptide compositions that include multiple epitopes of the TARP protein are described. The disclosed compositions can be used for the treatment of TARP-expressing cancers, such as prostate cancer, breast cancer and mesothelioma. In some embodiments, the TARP peptide compositions disclosed herein include sets of overlapping TARP peptides that each have a length of about 15 to about 25 amino acids, and comprise about 5 to about 15 amino acids that are identical to at least another overlapping peptide in the set. In particular examples, the combination of the overlapping TARP peptides in the set encompasses the complete amino acid sequence of human TARP. The multi-epitope peptide compositions described herein include both CD4 and CD8 epitopes, a feature that is important for eliciting CD4+ T cell and CD8+ T cell, as well as humoral, immune responses.

14 Claims, 1 Drawing Sheet
Specification includes a Sequence Listing.

(56) References Cited

OTHER PUBLICATIONS

Wolfgang et al., "TARP: A nuclear protein expressed in prostate and breast cancer cells derived from an alternate reading frame of the T cell Receptor γ chain locus," *Proc Natl Acad Sci USA* 97(17):9437-9442, 2000.

Wood, "Cancer Vaccines: Current Challenges & Evolving Concepts," Health Disparities Conference, University of Puerto Rico, oral presentation Apr. 13, 2013 (93 pages).

Wood, "Autologous TARP Peptide Vaccination is Associated with Slowing in PSA Velocity and a Decrease in Tumor Growth Rates in Patients with Stage D0 Prostate Cancer," AACR 2013 Annual Meeting, Abstract 4571, oral presentation Apr. 9, 2013 (18 pages).

Wood et al., "Therapeutic Vaccination with Epitope-Enhanced and Wild Type TARP Peptides in Stage Do Prostate Cancer," AACR 2011 Annual Meeting, Abstract 5520, poster presentation Apr. 6, 2011 (1 page).

Yamada et al., "Next-Generation Peptide Vaccines for Advanced Cancer," *Cancer Sci.*, vol. 104:15-21, 2013.

\* cited by examiner

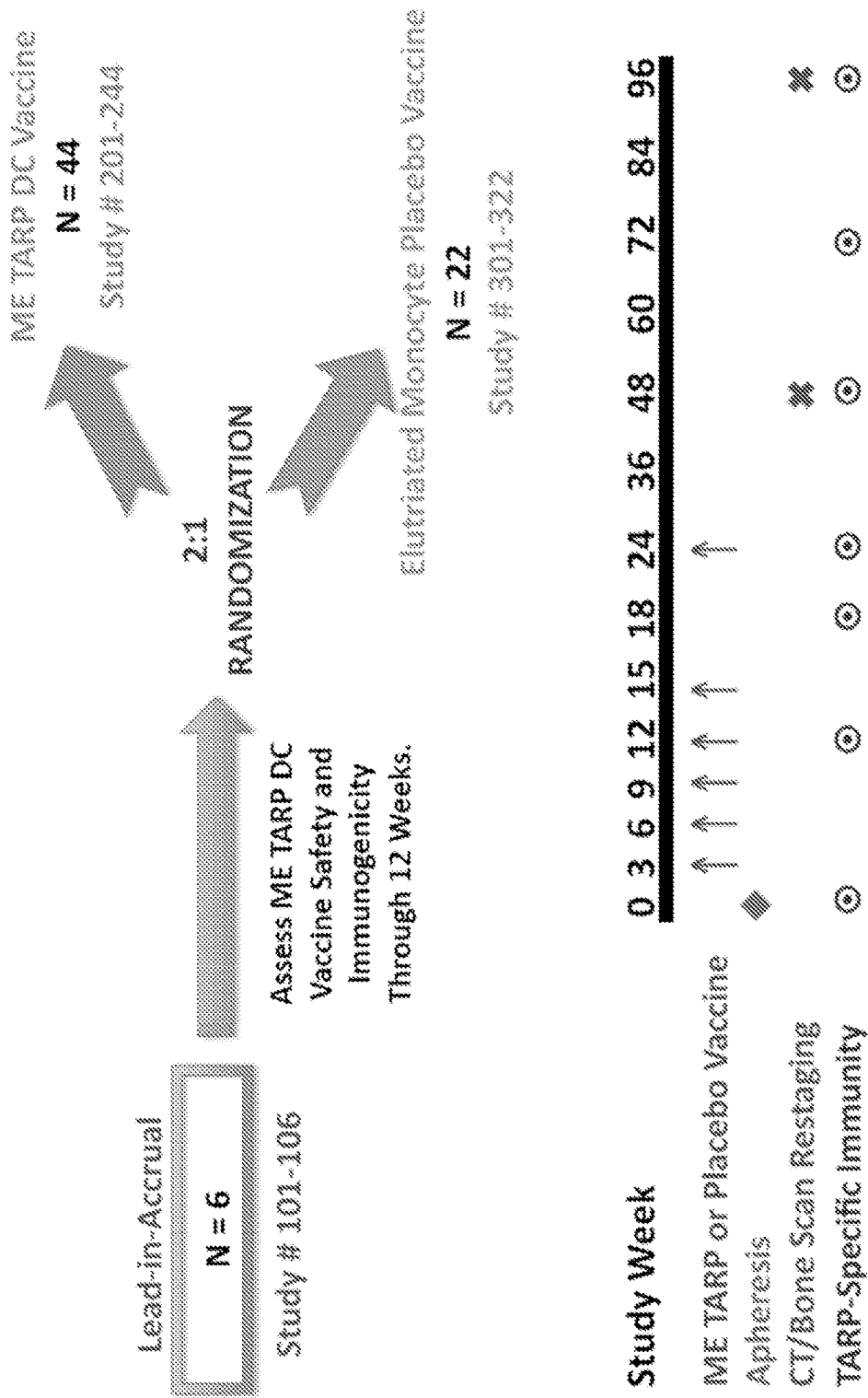

SEQUENCE LISTING

<160> NUMBER OF SEQ ID NOS: 10

<210> SEQ ID NO 1
<211> LENGTH: 58
<212> TYPE: PRT
<213> ORGANISM: Artificial Sequence
<220> FEATURE:
<223> OTHER INFORMATION: Synthetic peptide

<400> SEQUENCE: 1

Met Gln Met Phe Pro Pro Ser Pro Leu Phe Phe Phe Leu Gln Leu Leu
1               5                   10                  15

Lys Gln Ser Ser Arg Arg Leu Glu His Thr Phe Val Phe Leu Arg Asn
            20                  25                  30

Phe Ser Leu Met Leu Leu Arg Gly Ile Gly Lys Lys Arg Arg Ala Thr
        35                  40                  45

Arg Phe Trp Asp Pro Arg Gly Thr Pro
    50                  55

<210> SEQ ID NO 2
<211> LENGTH: 58
<212> TYPE: PRT
<213> ORGANISM: Homo sapiens

<400> SEQUENCE: 2

Met Gln Met Phe Pro Pro Ser Pro Leu Phe Phe Phe Leu Gln Leu Leu
1               5                   10                  15

Lys Gln Ser Ser Arg Arg Leu Glu His Thr Phe Val Phe Leu Arg Asn
            20                  25                  30

Phe Ser Leu Met Leu Leu Arg Tyr Ile Gly Lys Lys Arg Arg Ala Thr
        35                  40                  45

Arg Phe Trp Asp Pro Arg Gly Thr Pro
    50                  55

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Phe Val Phe Leu Arg Asn Phe Ser Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Phe Leu Arg Asn Phe Ser Leu Met Val
1               5

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

```
Met Gln Met Phe Pro Pro Ser Pro Leu Phe Phe Phe Leu Gln Leu Leu
1               5                   10                  15

Lys Gln Ser Ser
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Phe Phe Leu Gln Leu Leu Lys Gln Ser Ser Arg Arg Leu Glu His Thr
1               5                   10                  15

Phe Val Phe Leu
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

Arg Arg Leu Glu His Thr Phe Val Phe Leu Arg Asn Phe Ser Leu Met
1               5                   10                  15

Leu Leu Arg Gly
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

Arg Asn Phe Ser Leu Met Leu Leu Arg Gly Ile Gly Lys Lys Arg Arg
1               5                   10                  15

Ala Thr Arg Phe
            20

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide

<400> SEQUENCE: 9

Ile Gly Lys Lys Arg Arg Ala Thr Arg Phe Trp Asp Pro Arg Gly
1               5                   10                  15

Thr Pro

<210> SEQ ID NO 10
<211> LENGTH: 1027
<212> TYPE: DNA
<213> ORGANISM: Homo sapiens

<400> SEQUENCE: 10
gggcaagagt tgggcaaaaa aatcaaggta tttggtcccg gaacaaagct tatcattaca         60
```

```
gataaacaac ttgatgcaga tgtttccccc aagcccacta tttttcttcc ttcaattgct      120
gaaacaaagc tccagaaggc tggaacatac ctttgtcttc ttgagaaatt tttccctgat      180
gttattaaga tacattggca agaaaagaag agcaacacga ttctgggatc ccaggagggg      240
aacaccatga agactaacga cacatacatg aaatttagct ggttaacggt gccagaaaag      300
tcactggaca aagaacacag atgtatcgtc agacatgaga ataataaaaa cggagttgat      360
caagaaatta tctttcctcc aataaagacg gatgtcatca caatggatcc caagacaat       420 tgttcaaaag atgcaaatga tacactactg ctgcagctca caaacacctc tgcatattac      480
atgtacctcc tcctgctcct caagagtgtg gtctattttg ccatcatcac ctgctgtctg      540
cttagaagaa cggctttctg ctgcaatgga gagaaatcat aacagacggt ggcacaagga      600
ggccatcttt tcctcatcgg ttattgtccc tagaagcgtc ttctgaggat ctagttgggc      660
tttctttctg ggtttgggcc atttcagttc tcatgtgtgt actattctat cattattgta      720
taacggtttt caaaccagtg ggcacacaga gaacctcact ctgtaataac aatgaggaat      780
agccacggcg atctccagca ccaatctctc catgttttcc acagctcctc cagccaaccc      840
aaatagcgcc tgctatagtg tagacatcct gcggcttcta gccttgtccc tctcttagtg      900
ttctttaatc agataactgc ctggaagcct ttcattttac acgccctgaa gcagtcttct      960
ttgctagttg aattatgtgg tgtgtttttc cgtaataagc aaaataaatt taaaaaaatg     1020
aaaagtt                                                               1027
```

MULTI-EPITOPE TARP PEPTIDE VACCINE AND USES THEREOF

CROSS REFERENCE TO RELATED APPLICATIONS

This application is the U.S. National Stage of Internation Application No. PCT/US2014/070144, filed Dec. 12, 2014, published in English under PCT Article 21(2), which claims the benefit of U.S. Provisional Application No. 61/915,948, filed Dec. 13, 2013, which is herein incorporated by reference in its entirety.

FIELD

This disclosure concerns T cell receptor γ alternate reading frame protein (TARP) peptides and their use for stimulating an immune response against TARP-expressing cells, such as TARP-expressing tumor cells.

BACKGROUND

Historically five categories of tumor antigens have been utilized in immunotherapy: mutated antigens (e.g., p53 or RAS), over-expressed self-antigens (e.g., HER2/neu or MUC-1), differentiation antigens (e.g., gp100, tyrosinase), cancer testis antigens (e.g., MAGE, BAGE or CAGE families, NY-ESO-1) and viral antigens (e.g., HPV16 E6 or E7, EBV) (Cheever et al., *Clin Canc Res* 15:5323-5337, 2009). The advantages of therapeutic cancer vaccines utilizing proteins and peptides include the simplicity of production and the relative absence of major safety and regulatory issues.

All cells that express major histocompatibility complex (MHC) class I molecules can present short peptides (9-11 mers) from tumor-associated antigens (TAA) or viruses whose chronic persistent infection is associated with the development of malignancy (e.g. human papilloma virus, hepatitis B virus, and hepatitis C virus). However, co-stimulatory signals essential for T cell stimulation and the induction of lasting potent and effective immune responses are often absent due to the lack of induction of specific T-cell help, resulting in suboptimal and short-lived CD8$^+$ T-cell responses caused by a lack of proper T-helper cell-mediated signaling through dendritic cells (DCs) (Zom et al., *Adv Immunol* 114: 177-201, 2012). In addition, vaccination with restricted MHC class I binding peptides can be associated with induction of peptide-specific tolerance rather than tumor-controlling immunity (Toes et al., *J Immunol* 156: 3911-3918, 1996; Toes et al., *Proc Natl Acad Sci USA* 93:7855-7860, 1996). Furthermore, the use of a limited number of peptides within any given vaccine platform may allow the development of immune escape. Recent developments in therapeutic cancer vaccine research have included the use of TAA synthetic long peptides (SLPs) (Quakkelaar and Melief, *Adv Immunol* 114:77-106, 2012), as well as the use of overlapping and/or multi-epitope peptide vaccines (Walter et al., *Nat Med* 18:1254-1261, 2012). SLPs are synthetic peptides of 20-50 amino acids that because of their length require internalization and processing by DCs. Examples of multi-epitope peptide cancer vaccine platforms under clinical investigation include those using folate receptor alpha (NCT01606241), HER2/neu ((NCT01632332, NCT00266110, NCT00088985) and melanoma (NCTI00580060, NCT 00071981, NCT00471471, NCT00705640, NCTI00085137) peptides.

TARP (T-cell receptor γ alternate reading frame protein) is a 58 amino acid protein identified using the expressed sequence database (Maeda et al., *J Biol Chem.* 279:24561-24568, 2004). The mRNA is initiated in the Jγ 1 exon of the TCR γ and the protein expressed is initiated in an alternative reading frame distinct from that of the TCR γ coding sequence. Prior studies have shown that TARP is highly expressed in primary as well as metastatic prostate cancer; is expressed in prostate cancers with a range of Gleason patterns: and is expressed in both hormone sensitive and castrate resistant prostate cancer.

SUMMARY

Provided herein are compositions comprising immunogenic TARP peptides, and their use for eliciting an immune response in a subject, such as for the treatment of a TARP-expressing cancer.

In some embodiments, the composition includes at least two non-identical overlapping TARP peptides, wherein the amino acid sequences of the at least two overlapping TARP peptides consist of 15 to 25 consecutive amino acids of SEQ ID NO: 1 or SEQ ID NO: 2, and wherein each of the at least two overlapping TARP peptides comprises 5 to 15 consecutive amino acids that are identical to another of the overlapping TARP peptides. In some examples, the composition includes three, four, five, six or seven overlapping TARP peptides. In one non-limiting embodiment, the composition comprises five overlapping TARP peptides, wherein the amino acid sequences of the five overlapping TARP peptides consist of 18 to 20 consecutive amino acids of SEQ ID NO: 1, and wherein each of the five overlapping TARP peptides comprises 10 consecutive amino acids that are identical to at least one other of the overlapping TARP peptides, and wherein the combination of the five overlapping TARP peptides comprises all 58 amino acids of SEQ ID NO: 1. In some examples, the composition further comprises the TARP peptides of SEQ ID NO: 3 and SEQ ID NO: 4.

In some embodiments, the compositions comprise antigen presenting cells (APCs), such as dendritic cells, loaded with the TARP peptides. In some embodiments, the compositions comprise a pharmaceutically acceptable carrier and/or an adjuvant.

Also provided is a method of eliciting an immune response in a subject, by administering to the subject a therapeutically effective amount of a TARP peptide composition disclosed herein.

Further provided is a method of treating a subject having a TARP-expressing cancer, such as prostate cancer, breast cancer or mesothelioma, comprising selecting a subject having a cancer that expresses TARP, such as a prostate cancer, breast cancer or mesothelioma that expresses TARP, and administering to the subject a therapeutically effective amount of a TARP peptide composition disclosed herein. In some embodiments, the subject is administered APCs loaded with TARP peptides.

The foregoing and other objects, features, and advantages of the invention will become more apparent from the following detailed description, which proceeds with reference to the accompanying figures.

BRIEF DESCRIPTION OF THE DRAWINGS

FIG. 1 is a schematic illustrating the study design of a therapeutic multi-epitope TARP cancer vaccine phase II clinical trial.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jun. 7, 2016, 4.71 KB, which is incorporated by reference herein. In the accompanying sequence listing:

SEQ ID NO: 1 is the amino acid sequence of a human TARP protein comprising a glycine at position 40.

SEQ ID NO: 2 is the amino acid sequence of human TARP, deposited under GENBANK™ Accession No. AAG29337.

SEQ ID NO: 3 is the amino acid sequence of the TARP 27-35 peptide.

SEQ ID NO: 4 is the amino acid sequence of the TARP 29-37-9V peptide.

SEQ ID NO: 5 is the amino acid sequence of the TARP 1-20 peptide.

SEQ ID NO: 6 is the amino acid sequence of the TARP 11-30 peptide.

SEQ ID NO: 7 is the amino acid sequence of the TARP 21-40 peptide.

SEQ ID NO: 8 is the amino acid sequence of the TARP 31-50 peptide.

SEQ ID NO: 9 is the amino acid sequence of the TARP 41-58 peptide.

SEQ ID NO: 10 is the nucleotide sequence of human TARP, deposited under GENBANK™ Accession No. AF51103.

DETAILED DESCRIPTION

I. Abbreviations

APC antigen presenting cell
cGMP current good manufacturing practices
CTL cytotoxic T lymphocyte
DC dendritic cell
DLT dose limiting toxicity
DMSO dimethylsulfoxide
EE epitope enhanced
GM-CSF granulocyte macrophage colony stimulating factor
HLA human leukocyte antigen
ICS intracellular cytokine staining
IFN interferon
IL interleukin
KLH keyhole limpet hemocyanin
LPS lipopolysaccharide
ME multi-epitope
MHC major histocompatibility complex
PBL peripheral blood lymphocyte
PBMC peripheral blood mononuclear cell
PSA prostate specific antigen
PSADT PSA doubling time
PTFE polytetrafluoroethylene
rh recombinant human
SLP synthetic long peptide
TAA tumor-associated antigen
TARP T cell receptor γ alternate reading frame protein
TFA trifluoroacetic acid
TIL tumor infiltrating lymphocyte
WT wild type

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.). *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A vehicle used to enhance antigen presentation and stimulate an immune response, such as a suspension of minerals (alum, aluminum hydroxide, or phosphate) on which antigen is adsorbed; or water-in-oil emulsion in which antigen solution is emulsified in mineral oil (Freund's incomplete adjuvant), sometimes with the inclusion of killed mycobacteria (Freund's complete adjuvant) to further enhance immunogenicity (inhibits degradation of antigen and/or causes influx of macrophages). Imnmunostimulatory oligonucleotides (such as those including a CpG motif) can also be used as adjuvants (for example see U.S. Pat. Nos. 6,194,388; 6,207,646; 6,214,806; 6,218,371; 6,239,116; 6,339,068; 6,406,705; and 6,429,199). In one embodiment, the adjuvant is MONTANIDE® ISA 51 VG plus GM-CSF. In some embodiments, the adjuvant is a non-naturally occurring adjuvant.

Administration: The introduction of a composition into a subject by a chosen route. For example, if the chosen route is intravenous, the composition is administered by introducing the composition into a vein of the subject. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes. In particular embodiments disclosed herein, the route of administration is intradermal.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies and/or a CD4+ or CD8+ T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In some embodiments, T cells respond to the epitope, when the epitope is presented in conjunction with an MHC molecule.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. A disease-specific antigen is expressed coincidentally with a disease process. Specific non-limiting examples of a disease-specific antigen are an antigen whose expression correlates with, or is predictive of, tumor formation, such as prostate cancer or breast cancer. TARP is one example of a disease-specific antigen that is overexpressed in prostate cancer, breast cancer and other types of cancer. A disease-specific antigen can be an antigen recognized by T cells or B cells.

Antigen presenting cells (APCs): A type of cell that displays antigens complexed with major histocompatibility complex (MHC) proteins on their surface. Professional APCs are very efficient at internalizing antigen, processing it and then displaying small pieces of the antigen (peptides) bound to a MHC molecule on the cell membrane surface. The three main types of professional APCs include DCs, macrophages and certain B cells. DCs have the broadest range of antigen presentation and are the most important APC in processing antigens for presentation to T-cells, which recognize antigen-MHC complexes using their T cell receptors.

Autologous: Derived from the same individual. In the context of the present disclosure, "autologous" APCs used for treatment of a subject are APCs originally obtained from the subject.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Cancer: A malignant neoplasm that has undergone characteristic anaplasia with loss of differentiation, increased rate of growth, invasion of surrounding tissue, and is capable of metastasis. For example, prostate cancer is a malignant neoplasm that arises in or from prostate tissue, and breast cancer is a malignant neoplasm that arises in or from breast tissue (such as a ductal carcinoma). Residual cancer is cancer that remains in a subject after any form of treatment given to the subject to reduce or eradicate the cancer. Metastatic cancer is a cancer at one or more sites in the body other than the site of origin of the original (primary) cancer from which the metastatic cancer is derived.

CD4: Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8: Cluster of differentiation factor 8, a T cell surface protein that mediates interaction with the MHC Class I molecule. Cells that express CD8 are often cytotoxic T cells.

Chemotherapeutic agents: Any cytotoxic chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating prostate cancer, breast cancer or another tumor. In one embodiment, a chemotherapeutic agent is a radioactive compound. One of skill in the art can readily identify a chemotherapeutic agent of use (e.g., see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology 2$^{nd}$ ed., © 2000 Churchill Livingstone, Inc; Baltzer, L., Berkery, R. (eds): Oncology Pocket Guide to Chemotherapy. 2nd ed. St. Louis. Mosby-Year Book, 1995; Fischer. D. S., Knobf, M. F., Durivage. H. J. (eds): The Cancer Chemotherapy Handbook, 4th ed. St. Louis, Mosby-Year Book, 1993). Combination therapy is the administration of more than one agent, such as cytotoxic, radioactive or immunotherapeutic compounds, to treat cancer. One example is the administration of a TARP peptide vaccine used in combination with a radioactive or cytotoxic chemical compound.

Conservative variants: "Conservative" amino acid substitutions are those substitutions that do not substantially affect or decrease an activity or antigenicity of a protein, such as TARP. For example, a TARP polypeptide can include at most about 1, at most about 2, at most about 5, and most about 10, or at most about 15 conservative substitutions and specifically bind an antibody that binds the original TARP polypeptide. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variant also includes the use of a substituted amino acid in place of an unsubstituted parent amino acid. Non-conservative substitutions are those that reduce an activity or antigenicity.

Degenerate variant: A polynucleotide encoding an epitope of TARP that includes a sequence that is degenerate as a result of the genetic code. There are 20 natural amino acids, most of which are specified by more than one codon. Therefore, all degenerate nucleotide sequences are included in this disclosure as long as the amino acid sequence of the TARP peptide encoded by the nucleotide sequence is unchanged.

Dendritic cells (DCs): The principle professional antigen presenting cells (APCs) involved in primary immune responses. They are potent activators of T helper cell responses because as part of their composition, they express co-stimulatory molecules on their cell surface. Their major function is to obtain antigen in tissues, migrate to lymphoid organs and present the antigen in order to activate T cells. Immature dendritic cells originate in the bone marrow and reside in the periphery as immature cells. Dendritic cell sub-types include plasmacytoid dendritic cells and myeloid dendritic cells.

Consecutive: Following one after another in a series without interruption.

Contacting: Placement in direct physical association; includes both in solid and liquid form.

Epitope: An antigenic determinant. These are particular chemical groups or peptide sequences on a molecule that are antigenic, i.e. that elicit a specific immune response. An antibody specifically binds a particular antigenic epitope on a polypeptide.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain no internal stop codons.

Heterologous: Originating from separate genetic sources or species. For example, a polypeptide that is heterologous to TARP originates from a nucleic acid that does not encode TARP. In some embodiments, the heterologous amino acid sequence includes a protein tag, such as β-galactosidase, maltose binding protein, albumin, or an immunoglobulin amino acid sequence.

Immune response: A response of a cell of the immune system, such as a B cell, T cell, monocyte, macrophage, dendritic cell or natural killer cell to a stimulus. In one embodiment, the response is specific for a particular antigen (an "antigen-specific response"), also known as an adaptive immune response. In some embodiments, the adaptive immune response is a T cell response, such as a CD4+ response and/or a CD8+ response. In some embodiments, the adaptive immune response is a B cell response, and results in the production of specific antibodies.

Immunogenic peptide: A peptide which comprises an allele-specific motif or other sequence, such as an N-terminal repeat, such that the peptide will bind an MHC molecule and induce a CTL response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of MHC binding at a certain affinity that will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic composition: In the context of the present disclosure, a composition comprising a TARP polypeptide that induces a measurable CTL response against cells expressing TARP polypeptide, and/or induces a measurable B cell response (e.g. production of antibodies) against a TARP polypeptide. It further refers to isolated nucleic acid molecules encoding a TARP polypeptide that can be used to express the TARP polypeptide (and thus be used to elicit an immune response against this polypeptide). For in vitro use, the immunogenic composition may consist of the isolated protein or peptide. For in vivo use, the immunogenic composition will typically comprise the protein or peptide in pharmaceutically acceptable carriers, and/or other agents. Any particular peptide, TARP polypeptide, or nucleic acid encoding the polypeptide, can be readily tested for its ability to induce a CTL or B cell response by art-recognized assays. Immunogenic compositions can include adjuvants, which are well known to one of skill in the art.

Inhibiting or treating a disease: Inhibiting the full development of a disease or condition, for example, in a subject who is at risk for a disease such as a tumor (for example, a prostate or breast tumor). "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid or protein or organelle) has been substantially separated or purified away from other biological components in the cell of the organism in which the component naturally occurs, such as other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Linker: One or more nucleotides or amino acids that serve as a spacer between two molecules, such as between two nucleic acid molecules or two peptides (such as in a fusion protein).

Major histocompatibility complex (MHC): Generic designation meant to encompass the histocompatibility antigen systems described in different species, including the human leukocyte antigens ("HLA"). The term "motif" or "epitope" refers to the pattern of residues in a peptide of defined length, usually about 8 to about 11 amino acids, which is recognized by a particular MHC allele. The peptide motifs or epitopes are typically different for each MHC allele and differ in the pattern of the highly conserved residues and negative binding residues.

Mesothelioma: A type of neoplasm derived from the lining cells of the pleura and peritoneum which grows as a thick sheet covering the viscera, and is composed of spindle cells or fibrous tissue which may enclose gland-like spaces lined by cuboidal cells. Mesotheliomas often originate in the tissue lining the lung, heart or abdomen. In some cases, mesotheliomas are caused by exposure to asbestos.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Overlapping peptide: A peptide that at least partially overlaps in amino acid sequence with another peptide. In the context of the present disclosure. "overlapping TARP peptides" are peptides comprising a portion of the amino acid sequence of human TARP (SEQ ID NO: 1), wherein each overlapping TARP peptide contains about 5 to about 15 consecutive amino acids that are identical to at least one other overlapping TARP peptide in any given set of overlapping peptides. In some embodiments, the TARP peptides are 15 to 25 amino acids in length and have an amino acid sequence consisting of 15 to 25 consecutive amino acids of SEQ ID NO: 1. In particular examples, the set of overlapping TARP peptides contains all 58 amino acid residues of SEQ ID NO: 1.

Peptide or polypeptide: Any chain of amino acids regardless of length or post-translational modification (such as glycosylation or phosphorylation). In some embodiments, a polypeptide is between 5 and 100 amino acids in length, including 5 to 58, 5 to 50, 5 to 30, 8 to 20, 8 to 10, or 18 to 20 amino acids in length. In particular examples, a TARP polypeptide is 8, 9, 10, 18 or 20 amino acids in length.

A "TARP polypeptide" or "TARP peptide" is a series of contiguous amino acid residues from a TARP protein. In one example, with respect to immunogenic compositions comprising a TARP peptide, the term further refers to variations of these peptides in which there are conservative substitutions of amino acids, so long as the variations do not alter by more than about 20% (such as no more than about 1%, about 5%, or about 10%) the ability of the peptide to produce a B cell response, or, when bound to a MHC class I molecule, to activate cytotoxic T lymphocytes against cells expressing wild-type TARP protein. Induction of CTLs using synthetic peptides and CTL cytotoxicity assays are taught in. e.g., U.S. Pat. No. 5,662,907.

A "residue" refers to an amino acid or amino acid mimetic incorporated in a polypeptide by an amide bond or amide bond mimetic.

Peptide or polypeptide modifications: TARP peptides include synthetic embodiments of the peptides described herein. In addition, analogs (non-peptide organic molecules), derivatives (chemically functionalized peptide molecules obtained starting with the disclosed peptide sequences) and variants (homologs or paralogs) of these proteins can be utilized in the methods described herein. Each polypeptide is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the TARP peptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a TARP polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press, Buffalo Grove, Ill., pp. 165-174 and *Principles of Pharmacology* Munson (ed.) 1995, Ch. 102, for descriptions of techniques used in CADD. Also included are mimetics prepared using such techniques.

Polypeptide modifications also include amino acid substitutions, such as those that alter binding affinity of the polypeptide to MHC molecules. Exemplary amino acid substitutions for altering MHC binding affinity have been described in the art (see, for example, Berzofsky et al., *Nat. Rev. Immunol.* 1(3):209-219, 2001).

Pharmaceutically acceptable carrier: The pharmaceutically acceptable carriers of use are conventional. *Remington's Pharmaceutical Sciences*, by E. W. Martin. Mack Publishing Co., Easton, Pa., 15th Edition, 1975, describes compositions and formulations suitable for pharmaceutical delivery of proteins, such as those disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some embodiments, the pharmaceutical carrier is sterile, particularly when in an injectable form. In some embodiments, the pharmaceutical carrier is non-naturally occurring.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector: into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the retrovirus long terminal repeat; the adenovirus late promoter, the vaccinia virus 7.5K promoter) can be used. Promoters produced by recombinant DNA or synthetic techniques can also be used. A polynucleotide can be inserted into an expression vector or a viral vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Prostate Cancer: A malignant tumor, generally of glandular origin, of the prostate. Prostate cancers include adenocarcinomas and small cell carcinomas. Many prostate cancers express prostate specific antigen (PSA), prostate stem cell antigen (PSCA), PSMA (prostate specific membrane antigen), prostatic acid phosphatase (PAP) as well as other tumor antigens.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. A substantially purified protein is at least 60%, 70%, 80%, 90%, 95% or 98% pure. Thus, in one specific, non-limiting example, a purified protein is 90% free of other proteins or cellular components. The TARP polypeptides disclosed herein can be purified by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982).

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a TARP polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988: Higgins and Sharp, *CABIOS* 5:151, 1989; Corpet et al., *Nucleic Acids Research* 16:10881, 1988: and Pearson and Lipman, *Proc. Natl. Acad. Sci. U.S.A.* 85:2444, 1988. In addition, Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI. Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a TARP polypeptide are typically characterized by possession of at least about 75%, for example at least about 80%, 90%, 95%, 96%, 97%, 98% or 99% sequence identity counted over the full length alignment with the amino acid sequence of TARP or a TARP paralog using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Living multi-cellular vertebrate organisms, a category that includes both human and veterinary subjects, including human and non-human mammals.

Synthetic: Produced by artificial means in a laboratory, for example a synthetic nucleic acid or peptide can be chemically synthesized in a laboratory.

T cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. In another embodiment, a $CD4^+$ T cell is a regulatory T cell that also expresses CD25 and Foxp3 ("CD4+CD25+ regulatory T cells or Tregs"). $CD8^+$ T cells carry the "cluster of differentiation 8" (CD8) marker. In one embodiment. CD8+ T cells are cytotoxic T lymphocytes.

T cell receptor γ alternate reading frame protein (TARP): A polypeptide that is translated from a form of the T cell receptor γ gene. TARP is known to be expressed or overexpressed in several different types of cancer, including prostate cancer, breast cancer and mesothelioma. TARP is disclosed in PCT Publication No. WO 01/04309, which is incorporated herein by reference. Human TARP amino acid and nucleic acid sequences are set forth herein as SEQ ID NO: 1 and SEQ ID NO: 2 (protein), and SEQ ID NO: 10 (nucleic acid). TARP is also known as CD3G, TCRG, TCRGC1, TCRGC2, T-cell receptor gamma-chain constant region and TCR gamma alternate reading frame protein.

Therapeutically effective amount: A quantity of a specified agent sufficient to achieve a desired effect in a subject, cell or culture being treated with that agent. In the context of the present disclosure, a therapeutically effective amount of a TARP peptide is an amount of TARP peptide that causes induction of an immune response, as measured by clinical response (for example increase in a population of immune cells, production of antibody that specifically binds the peptide, or measurable reduction of tumor burden). In one embodiment, a therapeutically effective amount of a TARP peptide is an amount used to generate an immune response, or to treat cancer (such as breast cancer, mesothelioma or prostate cancer) in a subject.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Unit Dose: A drug or pharmaceutical composition in a single or metered dose form, such as a table, capsule, powder or solution to be administered as a single dose, or multiple preselected doses. In the context of the present disclosure, a TARP peptide composition in unit dose form contains a preselected therapeutic amount of peptide appropriate for a single dose, or one of multiple preselected metered doses, such as the amount necessary to elicit an immune response against TARP-expressing tumor cells. In some examples, the unit dose is a liquid contained in a sterile vial, or a powder in a sterile vial capable of being reconstituted for administration by introduction of a liquid into the vial. In other examples, the unit dosage form is provided in a syringe suitable for administration, for example injection into a subject.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments, the vector is a plasmid vector. In other embodiments, the vector is a viral vector.

Viable (cell): Alive and capable of growth and/or biological functions (such as antigen presentation, cytokine production etc.).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Multi-Epitope TARP Peptide Compositions

T cell receptor γ alternate reading frame protein (TARP) is a polypeptide that is translated from a form of the T cell receptor γ gene. TARP is known to be overexpressed in several types of cancer, including prostate cancer, breast cancer and mesothelioma. In particular, TARP is highly expressed in primary and metastatic prostate cancer, and in both hormone sensitive and castrate resistant prostate cancer. In addition, TARP expression is associated with unfavorable and more aggressive tumor behavior. Thus, TARP is an ideal tumor antigen for use in a cancer vaccine.

In one embodiment, the TARP protein has a sequence set forth as:

```
                                              (SEQ ID NO: 1)
         MQMFPPSPLFFFLQLLKQSSRRLEHTFVFL

RNFSLMLLRGIGKKRRATRFWDPRRGTP.
```

In another embodiment, the TARP protein has a sequence set forth as:

```
                                              (SEQ ID NO: 2)
         MQMFPPSPLFFFLQLLKQSSRRLEHTFVFL

RNFSLMLLRYIGKKRRATRFWDPRRGTP.
```

In other embodiments, TARP has an amino acid sequence at least 90% identical to SEQ ID NO: 1 or SEQ ID NO: 2, for example at least about 91%, 92%, 93%, 94%, 95%, 96%. 97%, 98%, or 99% identical to SEQ ID NO: 1 or SEQ ID NO: 2. Additional TARP variants have been described (see PCT Publication No. WO 01/04309, which is incorporated herein by reference).

In some embodiments, TARP is encoded by a nucleic acid having a sequence set forth as SEQ ID NO: 10.

In some embodiments, the TARP peptide compositions provided herein comprise at least one, such as two or more, overlapping TARP peptides selected from:

```
         TARP 1-20:
                                              (SEQ ID NO: 5)
         MQMFPPSPLFFFLQLLKQSS

TARP 11-30:
                                              (SEQ ID NO: 6)
         FFLQLLKQSSRRLEHTFVFL

TARP 21-40:
                                              (SEQ ID NO: 7)
         RRLEHTFVFLRNFSLMLLRG
```

```
TARP 31-50:
                                    (SEQ ID NO: 8)
RNFSLMLLRGIGKKRRATRF

TARP 41-58:
                                    (SEQ ID NO: 9)
IGKKRRATRFWDPRRGTP
```

The overlapping TARP peptides listed above are 18 or 20 amino acids in length and are HLA non-restricted.

In some embodiments, the overlapping TARP peptides are administered in combination with TARP 27-35 (FVFL-RNFSL; SEQ ID NO: 3) and/or the epitope enhanced TARP 29-37-9V (FLRNFSLMV; SEQ ID NO: 4), both of which are 9 mer peptides that bind HLA-A*0201.

A prospective, randomized pilot study of a first generation TARP peptide vaccine that utilized TARP 27-35 (SEQ ID NO: 3) and TARP 29-37-9V (SEQ ID NO: 4) peptides was previously conducted in HLA-A*0201 positive men with stage D0 prostate cancer (PSA biochemical recurrence without evidence of visceral or bony metastatic disease). TARP vaccination was found to be immunogenic, safe and well tolerated, with adverse events limited to injection site reactions. TARP vaccination was also associated with a decreased slope log PSA compared to pre-vaccination baseline in 72% of subjects reaching 24 weeks and in 74% of subjects reaching 48 weeks. The PSA slope or velocity is a validated measure of tumor growth in stage D0 prostate cancer in which there is no macroscopic tumor to measure. TARP vaccination also resulted in a 50% decrease in calculated tumor growth rate constant. TARP-specific interferon (IFN)-γ ELISPOT responses were detected in the majority of subjects but did not correlate with decreases in slope log (PSA).

The multi-epitope TARP peptide vaccine approach disclosed herein has several distinct advantages over previously reported TARP peptide vaccines. When all five overlapping TARP peptides are used, the peptides cover the entire TARP protein, resulting in potential for induction of a multivalent anti-TARP immune response, not limited to a single HLA type. In addition, the longer overlapping TARP peptides (18-20 amino acids in length) include TARP-specific MHC class II CD4+ T cell helper epitopes that allow for the generation of improved CD8+ T cell responses with enhanced functional avidity and longevity, as well as the induction of humoral anti-TARP antibody responses.

Provided herein are compositions that comprise at least two non-identical overlapping TARP peptides. In some embodiments, the amino acid sequences of the at least two overlapping TARP peptides consist of 15 to 25 consecutive amino acids of SEQ ID NO: 1 or SEQ ID NO: 2, and each of the at least two overlapping TARP peptides comprises 5 to 15 consecutive amino acids that are identical to at least another of the overlapping TARP peptides (for example, each of the at least two overlapping TARP peptides comprise 5 to 15 consecutive amino acids that are identical to 5 to 15 consecutive amino acids of at least another of the overlapping TARP peptides). In some examples, the at least two overlapping TARP peptides consist of 16 to 22, or 18 to 20 consecutive amino acids of SEQ ID NO: 1 or SEQ ID NO: 2. In particular examples, the at least two overlapping TARP peptides consist of 15, 16, 17, 18, 19, 20, 21, 22, 23, 24 or 25 consecutive amino acids of SEQ ID NO: 1 or SEQ ID NO: 2. In some examples, the overlapping TARP peptides comprise 8 to 12, or 9 to 11 consecutive amino acids that are identical to at least another of the overlapping TARP peptides. In particular examples, the at least two overlapping TARP peptides consist of 5, 6, 7, 8, 9, 10, 11, 12, 13, 14, 15, 16, 17, 18, 19 or 20 consecutive amino acids that are identical to at least one other of the overlapping TARP peptides.

In one non-limiting example, the at least two overlapping TARP peptides consist of 18 or 20 consecutive amino acids of SEQ ID NO: 1 or SEQ ID NO: 2, and each of the at least two overlapping TARP peptides comprises 10 consecutive amino acids that are identical to at least another of the overlapping TARP peptides (such as one or two of the other overlapping TARP peptides).

In some embodiments, the composition comprises three, four, five, six or seven overlapping TARP peptides. In particular examples, the composition comprises five overlapping TARP peptides.

In some embodiments, the combination of the three, four, five, six or seven overlapping TARP peptides comprises all 58 amino acids of SEQ ID NO: 1 or SEQ ID NO: 2.

In one non-limiting example, the composition comprises five overlapping TARP peptides, wherein the amino acid sequences of the five overlapping TARP peptides consist of 18 to 20 (such as 18 or 20) consecutive amino acids of SEQ ID NO: 1, and wherein each of the five overlapping TARP peptides comprises 10 consecutive amino acids that are identical to at least one other of the overlapping TARP peptides, and wherein the combination of the five overlapping TARP peptides comprises all 58 amino acids of SEQ ID NO: 1.

In some examples, the TARP peptide composition comprises at least two overlapping TARP peptides, wherein each peptide consists of a different amino acid sequence selected from SEQ ID NO: 5, SEQ ID NO: 6, SEQ ID NO: 7, SEQ ID NO: 8 and SEQ ID NO: 9.

In some embodiments, the TARP peptide compositions further include a TARP peptide consisting of SEQ ID NO: 3 and/or a TARP peptide consisting of SEQ ID NO: 4. In some examples, the composition comprises the TARP peptides of SEQ ID NO: 3, SEQ ID NO: 4, SEQ ID NO: 5, SEQ ID NO: 6, SEQ ID NO: 7, SEQ ID NO: 8 and SEQ ID NO: 9.

Also provided herein are compositions comprising polynucleotides encoding the TARP peptides disclosed herein. Such compositions can include polynucleotides encoding any combination of the TARP peptides disclosed herein. In some embodiments, the composition comprises a polynucleotide(s) encoding at least two overlapping TARP peptides having an amino acid sequence that consists of 15 to 25 consecutive amino acids of SEQ ID NO: 1 or SEQ ID NO: 2, wherein each of the at least two overlapping TARP peptides comprises 5 to 15 consecutive amino acids that are identical to at least one other of the overlapping TARP peptides. In some examples, the composition comprises a polynucleotide(s) encoding at least two overlapping TARP peptides selected from SEQ ID NO: 5, SEQ ID NO: 6. SEQ ID NO: 7, SEQ ID NO: 8 and SEQ ID NO: 9. In some examples, the compositions further include a polynucleotide(s) encoding the peptide of SEQ ID NO: 3 and/or the peptide of SEQ ID NO: 4. In particular examples, the polynucleotide comprises at least a portion of the nucleotide sequence of SEQ ID NO: 10. In some examples, the polynucleotides comprise vectors, such as plasmid vectors or viral vectors. Exemplary viral vectors include adenovirus vectors, adeno-associated virus vectors, retrovirus vectors and lentivirus vectors.

Polynucleotides include DNA, cDNA and RNA sequences which encode the peptide of interest. The polynucleotides encoding an immunogenic TARP peptide include recombinant DNA which is incorporated into a vector into an autonomously replicating plasmid or virus or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single-stranded and double-stranded forms of DNA.

A polynucleotide sequence encoding an immunogenic TARP peptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding an immunogenic TARP peptide can be inserted into an expression vector including, but not limited to, a plasmid, virus or other vehicle that can be manipulated to allow insertion or incorporation of sequences and can be expressed in a host cell. Methods of expressing DNA sequences having eukaryotic or viral sequences in prokaryotes are well known in the art. Biologically functional viral and plasmid DNA vectors capable of expression and replication in a host are known in the art.

In some embodiments, the compositions further include a pharmaceutically acceptable carrier. In some embodiments, the compositions further include an adjuvant. In some examples, particularly when the composition to be administered comprises isolated peptides, the adjuvant is MONTANIDE® ISA 51 VG, and may further include GM-CSF. In other examples, the adjuvant comprises poly-ICLC.

In some embodiments, the compositions comprise antigen presenting cells (APCs) loaded with the TARP peptides. In some examples, the APCs are professional APCs. In particular examples, the APCs are dendritic cells. APCs loaded with TARP peptide can be generated, for example, by pulsing or co-incubating APCs with the TARP peptides. Alternatively, APCs can be transduced with a vector encoding the TARP peptide. The TARP peptide will then be expressed and processed by the APC for presentation on the APC surface.

In some embodiments, the compositions are in unit dose form. In some examples, the composition in unit dose form comprises a lyophilized powder of the TARP peptides.

Immunogenic TARP peptides can be chemically synthesized by standard methods. If desired, polypeptides can also be chemically synthesized by emerging technologies. One such process is described in W. Lu et al., *Federation of European Biochemical Societies Letters*. 429:31-35, 1998. Polypeptides can also be produced using molecular genetic techniques, such as by inserting a nucleic acid encoding TARP or an epitope thereof into an expression vector, introducing the expression vector into a host cell, and isolating the polypeptide.

IV. Administration and Use of TARP Peptide Compositions

The immunogenic TARP peptides disclosed herein can be administered to a subject in order to generate an immune response. Thus, provided herein is a method of eliciting an immune response in a subject by administering to the subject a therapeutically effective amount of a TARP peptide composition disclosed herein. In some instances, the immune response comprises a CD4+ T cell response, a CD8+ T cell response, or both. The immune response can also include an anti-TARP antibody response. In some embodiments, the composition is administered intradermally, intramuscularly or subcutaneously.

The TARP peptide compositions disclosed herein can be administered to a subject to treat a cancer that expresses TARP, such as prostate cancer, mesothelioma, breast cancer, or any other tumor that expresses TARP. Thus, in some embodiments, the subject has prostate cancer, breast cancer or mesothelioma, or any other cancer that is identified to express or over-express TARP. In one example, the subject with breast cancer has triple-negative breast cancer. In one example, the subject with prostate cancer has hormone-sensitive prostate cancer. In another example, the subject with prostate cancer has castration-resistant prostate cancer. In some examples, the cancer is metastatic. In some examples, the immune response inhibits the growth of the TARP-expressing cancer. In some cases, the subject has undergone or will undergo other cancer-specific treatments, including surgery, chemotherapy or radiation therapy.

Also provided are methods of treating a subject with cancer, by selecting a subject with a cancer that expresses TARP, and administering to the subject a therapeutically effective amount of a TARP peptide composition disclosed herein. In some embodiments, the TARP-expressing cancer is prostate cancer, breast cancer or mesothelioma. In some embodiments, the composition is administered intradermally, intravenously, intramuscularly or subcutaneously.

In exemplary applications, the disclosed compositions are administered to a patient suffering from a disease, such as prostate cancer, mesothelioma, breast cancer, or any other cancer that expresses TARP, in an amount sufficient to raise an immune response to TARP-expressing cells. Administration induces a sufficient immune response to slow the proliferation of such cancer cells or to inhibit their growth, or to reduce a sign or a symptom of the tumor. Amounts effective for this use will depend upon the severity of the disease, the general state of the patient's health, and the robustness of the patient's immune system. A therapeutically effective amount of the composition is that which provides either subjective relief of a symptom(s) or an objectively identifiable improvement as noted by the clinician or other qualified observer, including alterations in laboratory parameters such as kinetics of PSA value change.

In some embodiments, the subject is HLA-A2 positive. In other embodiments, the subject is HLA-A2 negative.

In some embodiments, the compositions comprise antigen presenting cells (APCs), such as dendritic cells, loaded with the TARP peptides. In some examples, the APCs are autologous cells. In other examples, the APCs are allogeneic. In these methods, APCs can be pulsed or co-incubated with immunogenic TARP peptides in vitro. Alternative, the APCs can be transduced with a vector encoding the immunogenic TARP peptides, which leads to processing and display of the peptide in complex with MCH. Regardless of the method used to generate APCs loaded with TARP peptides, a therapeutically effective amount of the APCs can then be administered to a subject. In some examples, the therapeutically effective amount of the composition comprises about $1 \times 10^6$ to about $30 \times 10^6$ viable APCs, such as about $5 \times 10^6$ to about $25 \times 10^6$ viable APCs, or about $10 \times 10^6$ to about $20 \times 10^6$ viable APCs. In non-limiting examples, the therapeutically effective amount of the composition comprises about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $10 \times 10^6$, $15 \times 10^6$, $20 \times 10^6$, $25 \times 10^6$, or $30 \times 10^6$ viable APCs. In some cases, when multiple peptides are to be administered to a subject using APCs, individual pools of cells are each pulsed with one peptide and subsequently pooled together for administration. The pooled APCs can be administered in a single injection, or in multiple injections, such as in two injections. In most cases, the peptide-loaded APCs are administered intradermally, but can be administered using any suitable route for generating an immune response, such as subcutaneously, intravenously or intramuscularly.

As discussed above, the immunogenic TARP peptide(s) can be delivered to the dendritic cells or to dendritic cell precursors via any method known in the art, including, but not limited to, pulsing dendritic cells directly with antigen, or utilizing a broad variety of antigen delivery vehicles, such as, for example, liposomes, or other vectors known to deliver antigen to cells. In one specific, non-limiting example an antigenic formulation includes about 0.1 µg to about 1,000 µg, or about 1 to about 100 µg of a selected immunogenic TARP peptide. The immunogenic TARP peptide can also be administered with agents that promote dendritic cell maturation. Specific, non-limiting examples of agents of use are interleukin-4 (IL-4), interferon-gamma (IFN-γ), endotoxin/lipopolysaccharide (LPS), keyhole limpet hemocyanin (KLH), granulocyte/macrophage colony stimulating factor (GM-CSF), or flt-3 ligand (flt-3L). The preparation can also contain buffers, excipients, and preservatives, amongst other ingredients.

In one embodiment, mature antigen presenting cells are generated to present the immunogenic TARP peptide(s). These dendritic cells are then administered alone to a subject with a tumor that expresses TARP, such as a prostate cancer, mesothelioma or breast cancer. In another embodiment, the mature dendritic cells are administered in conjunction with a chemotherapeutic agent or other immune-based therapies targeting negative regulation such as anti-CLA-4 (cytotoxic T-lymphocyte antigen 4), anti-PD-1 (programmed cell death protein 1) or anti-PD-L1 (programmed cell death 1 ligand 1).

Alternatively, the APCs are used to sensitize CD8+ cells, such as tumor infiltrating lymphocytes (TILs) from prostate, mesothelioma or breast tumors (or another type of cancer) or peripheral blood lymphocytes (PBLs). The TILs or PBLs can be from the same subject (autologous) that is to be treated. Alternatively, the TILs or PBLs can be heterologous. However, they should at least be MHC class-I restricted to the HLA types the subject possesses. An effective amount of the sensitized cells are then administered to the subject.

Peripheral blood mononuclear cells (PBMCs) can be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived, such as TARP (e.g. SEQ ID NO: 1 or SEQ ID NO: 2).

The cells can be administered to a subject to inhibit the growth of cells of TARP expressing tumors. In these applications, a therapeutically effective amount of activated antigen presenting cells, or activated lymphocytes, are administered to a subject suffering from a disease, in an amount sufficient to raise an immune response to TARP-expressing cells. The resulting immune response is sufficient to slow the proliferation of such cancer cells or to inhibit their growth, or to reduce a sign or a symptom of the tumor.

In other embodiments, compositions comprising isolated TARP peptides are administered to the subject. An immunogenic TARP peptide can be administered by any means known to one of skill in the art (see Banga. A., "Parenteral Controlled Delivery of Therapeutic Peptides and Proteins." in *Therapeutic Peptides and Proteins*, Technomic Publishing Co., Inc., Lancaster, Pa., 1995) such as by intradermal, intramuscular, subcutaneous, or intravenous injection. In one embodiment, administration is by intradermal or intramuscular injection. To extend the time during which the peptide(s) is available to stimulate a response, the peptide(s) can be provided as an implant, an oily injection, or as a particulate system. The particulate system can be a microparticle, a microcapsule, a microsphere, a nanocapsule, or similar particle. A particulate carrier based on a synthetic polymer has been shown to act as an adjuvant to enhance the immune response, in addition to providing a controlled release. Aluminum salts can also be used as adjuvants to produce an immune response.

In some embodiments, an immunogenic TARP peptide composition is administered in a manner to direct the immune response to a cellular response (that is, a CTL response). A number of means for inducing cellular responses, both in vitro and in vivo, are known. Lipids have been identified as agents capable of assisting in priming CTLs in vivo against various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide that displays an appropriate epitope, two compositions can be combined to elicit both humoral and cell-mediated responses where that is deemed desirable.

In another embodiment, to induce a CTL response to an immunogenic TARP peptide composition, a MHC class II-restricted T-helper epitope is added to the immunogenic TARP polypeptide to induce T-helper cells to secrete cytokines in the microenvironment to activate CTL precursor cells. The overlapping TARP peptides disclosed herein include MHC class II epitopes for inducing T-helper cells. The technique further involves adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Immunotherapeutics to Treat Infectious Diseases and Cancer," in Powell et al., eds., *Vaccine Design, the Subunit and Adjuvant Approach*, Plenum Press, New York. 1995).

Pharmaceutical compositions including immunogenic TARP peptides are provided herein. In one embodiment, the immunogenic TARP peptides are mixed with an adjuvant containing a stabilizing detergent, a micelle-forming agent, and/or an oil. In one embodiment, the adjuvant is MONTANIDE® ISA 51 VG, and may further include granulocyte macrophage colony stimulating factor (GM-CSF). Suitable stabilizing detergents, micelle-forming agents, and oils are detailed in U.S. Pat. No. 5,585,103; U.S. Pat. No. 5,709,860; U.S. Pat. No. 5,270,202: and U.S. Pat. No. 5,695,770. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion (i.e., to provide a vehicle for the desired antigen) and may have a melting temperature of less than 65° C. such that an emulsion is formed either at room temperature (about 20° C. to 25° C.), or once the temperature of the emulsion is brought down to room temperature. Examples of such oils include squalene, squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse effects, such as granulomas, are evident upon use of the oil.

An adjuvant can be included in the composition. In one embodiment, the adjuvant is MONTANIDE® ISA 51 VG plus GM-CSF. In other embodiments, the adjuvant is a mixture of stabilizing detergents, micelle-forming agent, and oil available under the name PROVAX® (Biogen Idec, San Diego, Calif.). An adjuvant can also be an immunostimulatory nucleic acid, such as a nucleic acid including a CpG motif.

In another embodiment, the TARP composition includes one or more nucleic acids encoding one or more immunogenic TARP peptides. A therapeutically effective amount of the nucleic acid(s) encoding the TARP peptide(s) can be administered to a subject in order to generate an immune response. In one specific, non-limiting example, a therapeutically effective amount of the nucleic acid(s) is administered to a subject to treat prostate cancer, mesothelioma or breast cancer, or any other tumor that expresses TARP. One approach to administration of nucleic acids to a subject is direct immunization with plasmid DNA, such as with a mammalian expression plasmid. The nucleotide sequence encoding an immunogenic TARP peptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and QUIL A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce MHC class 1 mediated CTL responses (Takahashi et al., *Nature* 344:873, 1990).

In another approach to using nucleic acids for immunization, immunogenic TARP peptides can be expressed by attenuated viral hosts or vectors or bacterial vectors. Recombinant vaccinia virus, adeno-associated virus, herpes virus, retrovirus, or other viral vectors can be used to express the peptide, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In one embodiment, one or more nucleic acids encoding one or more immunogenic TARP peptides are introduced directly into cells. For example, the nucleic acid(s) can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 µg/kg to about 50 mg/kg, and typically are about 0.005 mg/kg to about 5 mg/kg (see, e.g., U.S. Pat. No. 5,589,466).

The compositions (e.g., TARP peptides. APCs loaded with TARP peptides, or nucleic acids or vectors encoding TARP peptides) can be administered for therapeutic treatments. In therapeutic applications, a therapeutically effective amount of the composition is administered to a subject suffering from a disease, such as prostate cancer, mesothelioma or breast cancer, or any other cancer that expresses TARP. Single or multiple administrations of the compositions are administered depending on the dosage and frequency as required and tolerated by the subject. In one embodiment, the composition is administered in multiple doses, such as two, three, four, five, six, seven or eight doses. Generally, the dose is sufficient to treat or ameliorate symptoms or signs of disease without producing unacceptable toxicity to the subject. Systemic or local administration can be utilized. For each dose, the composition can be administered using a single injection (a single site of injection) or can be administered using two or more injections (two or more sites of injection). In particular examples, the TARP peptide compositions are administered using two injections (such as one in each arm). In other cases, particularly if isolated TARP peptides are being administered (i.e. administered in the absence of APCs), one site per peptide may be required.

In some embodiments, any of the immunotherapies discussed above is augmented by administering a cytokine, such as IL-2, IL-3. IL-6, IL-10, IL-12, IL-15, GM-CSF, or interferons, or a combination of two or more cytokines, such as 2, 3, 4, 5, 6, 7 or more cytokines.

Administration of the immunogenic TARP peptide compositions disclosed herein can also be accompanied by administration of other anti-cancer agents or therapeutic treatments (such as surgical resection of a tumor). Any suitable anti-cancer agent can be administered in combination with the compositions disclosed herein. Exemplary anti-cancer agents include, but are not limited to, cytotoxic chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy, antibodies that specifically target cancer cells, or antibodies to other immune modulating proteins such as CTLA-4, PD-1, PD-L1 or TGF-β (transforming growth factor-beta).

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCN LU, Carboplatinum, Cis-platinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin®, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute). IL-2 (Cetus or Hoffman-LaRoche), human immune globulin (Cutter Biological). IMREG (from Imreg of New Orleans, La.), SK&F 106528. TNF (tumor necrosis factor; Genentech) and anti-CTLA-4 (ipilimumab, Bristol-Myers Squibb).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

In particular embodiments, a subject having prostate cancer is administered a TARP peptide composition disclosed herein in combination with radiation therapy, brachytherapy, or cryotherapy. In other specific embodiments, a subject having prostate cancer, such as metastatic castration-resistant prostate cancer, is administered a TARP peptide composition disclosed herein in combination with chemotherapy.

In other embodiments, a subject with a TARP-expressing cancer, such as prostate cancer, is administered a TARP peptide composition disclosed herein in combination with an agent that targets negative regulation of the immune system, such as anti-CTLA4, anti-PD-1, anti-PD-L1 or anti-TGFβ.

V. Wild-Type and Epitope-Enhanced TARP Peptides as Cancer Vaccines

Two HLA-A2 epitopes that produce cytolytic T cell responses were previously identified (Oh et al., *Cancer Res.* 64:2610-2618, 2004). These sequences map to amino acids 27-35 and 29-37 of human TARP (SEQ ID NO: 2). TARP 27-35 was found to bind with an affinity that was 10 times greater than that of TARP 29-37. Both peptides were shown to be immunogenic by immunizing A2K$^b$ transgenic mice (expressing human HLA-A*0201) with dendritic cells pulsed with the peptides or with DNA encoding the peptides. Dendritic cell immunization produced a higher level of immunity than DNA immunization, and as expected due to its higher binding affinity, TARP 27-35 produced a higher level of CD8+ T cell response than TARP29-37.

A. Epitope Enhancement

Modification of the amino acid sequence of epitopes, commonly referred to as epitope enhancement, can improve the efficacy of vaccines through several means: (1) increasing affinity of peptide for MHC molecules; (2) increasing T cell receptor (TCR) triggering; or (3) inhibiting proteolysis of the peptide by serum peptidases. Epitope-enhanced subdominant peptides can bypass self-tolerance because subdominant epitopes do not generally induce tolerance but can be made more immunogenic by epitope enhancement.

Epitope enhancement of TARP peptides was previously performed to increase the level of immunity that could be generated with these peptides. As described in U.S. Pat. Nos. 7,541,035 and 8,043,623 (incorporated herein by reference), amino acid substitutions in the TARP 27-35 peptide did not increase binding affinity, but two amino acid substitutions in TARP 29-37 did produce higher binding affinity peptides. For TARP 29-37, Arg at position 3 and Leu at position 9 were substituted with Ala (TARP 29-37-3A) and Val (TARP 29-37-9V), respectively. Substitution at position 3 with Ala in TARP 29-37 resulted in the greatest increase in the binding affinity of the peptide. Although TARP29-37-9V showed a lower binding affinity to HLA-A2 than TARP29-37-3A, substitution of Leu at position 9 with Val did enhance the binding affinity compared with the wild-type peptide, TARP 29-37. When the immunogenicity of these peptides was evaluated in A2K$^b$ transgenic mice, both of the epitope-enhanced peptides produced a higher percentage of TARP-specific CD8$^+$ T cells than the wild type sequence. It was also shown that T cells generated with the epitope-enhanced TARP 29-37 sequences reacted with targets pulsed with the wild type TARP 29-37 peptide in the mouse.

Studies of these peptides in human cells showed that TARP 29-37, TARP 29-37-3A, and TARP 29-37-9V were immunogenic in human T cells. TARP 29-37-9V specific T cells recognized targets pulsed with all three peptides equally well, whereas TARP 29-37-3A specific T cells recognized only targets pulsed with TARP 29-37-3A. This suggested that the TARP 29-37-3A peptide would not be appropriate for immunization in humans, whereas the TARP 29-37-9V would be more likely to generate T cells that recognize the wild type sequence. Human T cells specific for TARP 27-35 recognized targets pulsed with that sequence. In addition to their ability to kill targets pulsed with TARP peptides. CD8$^+$ T cells specific for TARP peptides were able to kill human tumor targets that were HLA-A2 positive and that expressed TARP sequences, confirming that TARP was endogenously processed and presented in human tumor cells. The availability of tetramers that react with CD8$^+$ T cells specific for TARP provided a simple means of evaluating the ability to stimulate immunity to the TARP peptides. In one survey, tetramer positive cells ranged from 0.66% to 3.9% of the CD8$^+$ T cells in prostate and breast cancer patients compared with 0.01-0.6% in normal controls.

B. Therapeutic Vaccination Utilizing Wild Type (WT) and Epitope-enhanced (EE) TARP Peptides (NCI 09-C-0139)

NCI 09-C-0139 is a prospective, randomized pilot clinical study examining TARP vaccination in HLA-A*0201 positive men with Stage D0 prostate cancer (PSA biochemical recurrence without evidence of visceral or bony metastatic disease). Since the optimal method for therapeutic immunization with peptide vaccines in patients with cancer is unclear, patients were randomized to receive vaccination with TARP peptides in MONTANIDE® ISA 51 VG adjuvant plus GM-CSF (Arm A) or as an autologous, TARP peptide-pulsed dendritic cell (DC) vaccine. The primary objective was to determine the safety and immunogenicity (as measured by IFN-γ ELISPOT, intracellular cytokine staining (ICS) and tetramer assays) of TARP vaccination. The secondary objectives were to determine the effect of TARP peptide vaccination on PSA doubling time (PSADT) (Arlen et al., *J Urol* 179:2181-2186, 2008) and PSA growth rate and regression rate constants. All study participants had to have a baseline PSADT (calculated using PSA values within 12 months of study entry)>3 months and ≤15 months.

TARP vaccine was administered by deep subcutaneous injection (Arm A) or intradermally (Arm B, 20×10$^6$ viable cells/vaccine) at Weeks 3, 6, 9, 12, and 15, with an optional sixth dose of vaccine at Week 36 based on changes in PSADT (≥50% increase over pre-vaccine PSADT) or immune parameters (3-fold increase in TARP-specific reactivity as measured by IFN-γ ELISPOT at least two time points) at Week 24. TARP vaccination was found to be safe and well tolerated, with adverse events limited to injection site reactions≤Grade 2. There were no systemic or immediate hypersensitivity reactions or laboratory abnormalities associated with vaccination. TARP vaccination was also shown to be associated with a slowing in the rise of PSA levels (PSA velocity), measured as PSA doubling time (PSADT) or slope log (PSA), a surrogate marker for clinical outcomes and how well patients will do. A highly statistically significant decrease was observed in the slope log PSA (i.e. there was significant slowing in how fast the patients' PSAs were rising compared to their pre-vaccination baseline at both 3-24 and 3-48 weeks). In addition, this effect of decreased slope log (PSA)/slowing in PSA velocity at Weeks 3-24 didn't wane significantly over time and wasn't impacted by an additional vaccine dose at Week 36.

C. Multi-Epitope (ME) TARP Vaccine Design

The second generation ME TARP vaccine is based on the amino acid sequence of the entire TARP protein (SEQ ID NO: 1). The vaccine platform includes the original two 9-mer HLA-A*0201 binding TARP peptide epitopes (WT TARP 27-35 and EE TARP 29-37-9V) utilized in NCI 09-C-0139 as well as an additional five 20-mer TARP peptides overlapping by 10 amino acids for a total of 7 peptides that span the entire TARP sequence.

SLPs are synthetic peptides of 20-50 amino acids that because of their length require internalization and processing by DCs. Processing by these professional antigen presenting cells avoids presentation by non-professional antigen-presenting cells that could potentially induce tolerance instead of immunity. Overlapping SLPs contain both CD4 and CD8 epitopes, which results in parallel stimulation of both CD4+ and CD8+ T cells and a stronger, more effective immune response. In addition, since overlapping SLPs contain all potential epitopes irrespective an individual's MHC type, the use of SLPs is a highly attractive approach to maximize the therapeutic applicability of any given vaccine in a genetically diverse human population such as that of the United States. Protein vaccination is highly suitable for the induction of CD4+ T cell responses and antibodies, but it generally induces responses against dominant epitopes and often fails to induce proper and effective CD8+ T cell immunity, in contrast to long peptides that induce both. In addition, processing and uptake of SLPs by DCs is more efficient compared to processing and uptake of intact protein. For these reasons, SLPs and multi-epitope vaccines are able to induce a broader repertoire of T cell responses, thereby maximizing the diversity of epitopes potentially associated with anti-tumor effector function while minimizing the risk of tumor antigen escape.

The advantage of the multi-epitope TARP peptide vaccine platform disclosed herein is that the overlapping epitopes cover the entire TARP protein, eliminating the need for HLA restriction, thus allowing any and all patient populations with a TARP-expressing tumor to be candidates for therapeutic vaccination. In addition, these longer synthetic peptides include MHC class II CD4+ T cell helper epitopes that will allow generation of better CD8+ T cell responses with improved functional avidity and longevity as well as humoral anti-TARP antibody responses. The peptide sequences encompassing the whole protein will have all the possible epitopes that can be presented by any HLA molecule and therefore would be suitable for vaccinating the entire population of prostate cancer patients, making adequate accrual feasible. Overlapping long peptides, such as the 20-mers overlapping by 10 residues, have been used to represent a whole protein because they contain all the potential epitopes of the whole protein but are more amenable to processing for both class I and class II HLA presentation to CD4$^+$ and CD8$^+$ T cells (Jiang et al., *Vaccine* 24:6356-6365, 2006; Mirshahidi et al., *Vaccine* 27:1825-1833, 2009: Dong et al., *Vaccine* 23:3630-3633, 2005; Zhang et al., *J Biol Chem* 284:9184-9191, 2009).

The following examples are provided to illustrate certain particular features and/or embodiments. These examples should not be construed to limit the disclosure to the particular features or embodiments described.

EXAMPLES

Example 1

A Randomized, Placebo-Controlled Phase II Study of Multi-Epitope TARP (ME TARP) Peptide Autologous Dendritic Cell Vaccination in Men with Stage D0 Prostate Cancer Study Design Eligible patients are prospectively randomized 2:1 to receive either autologous TARP multi-epitope DC vaccine or an autologous elutriated monocyte vaccine placebo after safety and immunogenicity have been established through 12 weeks in an initial lead-in cohort of 6 patients as outlined in FIG. 1. Enrollment of this lead-in cohort is staggered every three weeks for the first three patients to allow a 3-week interval for safety assessment before the next enrolled patient is scheduled to receive their first dose of ME TARP vaccine. If there is no adverse safety signal identified in these first 3 patients, enrollment of the remaining 3 lead-in subjects and subsequent randomization of study subjects proceeds on or after 9 weeks after the first study subject has received their first ME TARP vaccine dose and 3 weeks after the third study subject has received their first ME TARP vaccine dose. All patients receive a total of 6 doses of vaccine ($20 \times 10^6$ viable cells/dose) delivered intradermally at Weeks 3, 6, 9, 12, 15, and 24. All patients undergo restaging at Weeks 48 and 96 to confirm maintenance of Stage D0 disease. The study monitoring schedule of clinical assessments, laboratory and imaging studies is identical for all patients as outlined in FIG. 1.

All patients have a history and physical exam, routine monitoring labs. PSA and testosterone levels performed at the study week visits shown in FIG. 1. PSA Doubling Time (PSADT) and slope log (PSA) are calculated at every study visit using the PSADT Memorial Sloane Kettering nomogram (available online). Immunologic responses (IFN-γ ELISPOT, ICS and tetramer assays, anti-TARP antibodies) to multi-epitope TARP peptide vaccination are examined at the following timepoints: Weeks 0, 12, 18, 24, 48, 72 and 96.

Vaccine Administration

All patients undergo 15-18 L apheresis to remove peripheral blood monocytes for dendritic cell preparation as well as peripheral blood mononuclear cells for flow cytometry and immunologic studies at their Week 0 visit. Cells used for subsequent dendritic cell maturation are derived from monocytes frozen during the initial apheresis. Eligible subjects receive autologous ME TARP dendritic cell or elutriated monocyte placebo vaccine beginning at Week 3. For patients receiving active ME TARP DC vaccine, each peptide is pulsed on dendritic cells separately in order to assure adequate binding of the peptide and cells are not washed to remove free peptide after pulsing. Following verification of mature dendritic cell validation markers and release standards, the separately peptide-pulsed dendritic cells are recombined for administration.

Autologous ME TARP DC and elutriated monocyte placebo vaccine preparations are assessed for release standards (nucleated cell content and concentration, appearance, flow cytometric verification of DC validation markers, viability≥60%, and product sterility and safety testing) prior to release for vaccine administration to the patient.

For both groups, vaccines are administered intradermally in two vaccination sites on the forearm with a maximum volume of 0.5 ml per injection. Vaccination is alternated between the left and right forearm with each vaccination. All patients receive a total of 6 doses of vaccine ($20 \times 10^6$ viable cells/dose) delivered at Weeks 3, 6, 9, 12, 15, and 24 and undergo restaging at Weeks 48 and 96 to confirm maintenance of Stage D0 disease.

Patients are monitored for immediate adverse event vaccine reactions for 1 hour following their first TARP peptide vaccine dose. If no adverse reactions are observed with the first vaccination, patients are monitored for 15 minutes for all subsequent vaccinations.

If an adverse reaction is observed following the first vaccine, the reaction is characterized and a determination made as to whether it is considered a dose limiting toxicity (DLT). If the adverse reaction is determined not to be a DLT, the duration of post-vaccination monitoring for subsequent vaccinations is determined as clinically indicated depending on the severity of the initial vaccine reaction.

All patients are given a ME TARP DC Vaccine Report Card and instructed on how to complete it, following each ME TARP DC or placebo vaccine dose.

Since this protocol involves multi-epitope TARP vaccination in humans for the first time, enrollment of randomized subjects does not begin until safety and immunogenicity through 12 weeks are established in an initial staggered enrollment lead in of 6 patients. If no adverse events are observed through Week 12 following the first vaccination in these 6 patients, enrollment of additional patients may proceed as quickly as is logistically feasible.

Autologous Multi-Epitope (ME) TARP Dendritic Cell Vaccine Description

The $2^{nd}$ generation ME TARP vaccine is based on the amino acid sequence of the entire TARP protein (SEQ ID NO: 1). The vaccine platform includes the original two 9-mer HLA-A*0201 binding TARP peptide epitopes (WT TARP 27-35 and EE TARP 29-37-9V) utilized in NCI 09-C-0139 as well as an additional five 20-mer TARP peptides overlapping by 10 amino acids for a total of 7 peptides that span the entire TARP sequence:

```
TARP 27-35:
(SEQ ID NO: 3; HLA-A*0201 restricted)
FVFLRNFSL

TARP 29-37-9V:
(SEQ ID NO: 4; HLA-A*0201 restricted)
FLRNFSLMV

TARP 1-20:
(SEQ ID NO: 5; HLA non-restricted)
MQMFPPSPLFFFLQLLKQSS;

TARP 11-30:
(SEQ ID NO: 6; HLA non-restricted)
FFLQLLKQSSRRLEHTFVFL

TARP 21-40:
(SEQ ID NO: 7; HLA non-restricted)
RRLEHTFVFLRNFSLMLLRG

TARP 31-50:
(SEQ ID NO: 8; HLA non-restricted)
RNFSLMLLRGIGKKRRATRF

TARP 41-58:
(SEQ ID NO: 9; HLA non-restricted)
IGKKRRATRFWDPRRGTP
```

Autologous ME TARP DC vaccine and autologous elutriated monocyte placebo vaccine are generated utilizing current good manufacturing practices (cGMP) as outlined in Example 2.

Study Drugs

Interleukin-4 CELLGENIX™

Product Description: Interleukin-4 (IL-4) used in this study is manufactured and supplied by CellGenix (Freiburg, Germany). It is used as an ancillary product to mature dendritic cells in vitro and is not administered directly to patients. IL-4 exerts important effects on B cells, T cells, macrophages, eosinophils, hematopoietic progenitor cells, endothelial cells and promotes the maturation of dendritic cells. The complementary DNA clone (cDNA), when expressed in E. coli yields a 129 amino acid protein with a molecular weight of 14,957 daltons. IL-4 is a highly purified (≥95% chromatographically pure), sterile, water-soluble protein.

Formulation and Preparation: RhIL-4 Sterile Powder for Injection is supplied in 100 mcg and 200 mcg vials (containing a total of 120 mcg and 240 mcg of IL-4, respectively) as a sterile lyophilized powder formulated with glycine, human serum albumin, citric acid, and sodium citrate. Unreconstituted IL-4 is kept refrigerated at 2-8° C. 1.2 mL of Sterile Water for Injection USP is added to each vial of rhIL-4 Sterile Powder for Injection. The vial is gently agitated to completely dissolve the powder and is inspected visually for discoloration and particulates prior to use.

Stability and Storage: The reconstituted product is refrigerated at 2-8° C. and used within 24 hours.

Administration Procedures: To be used in dendritic cell culture, not administered directly to patients.

KLH (Keyhole Limpet Hemocyanin)

Product Description: Stellar Biotechnology's KLH is a potent form of clinical grade KLH that is manufactured by Sigma-Aldrich. It is purified from the hemocyanin of the giant keyhole limpet, Megathura crenulata. The denatured subunit of KLH is a glycoprotein with a molecular weight of 400-450,000 daltons. The native form of KLH is a dodecamer, which consists of twenty (20) subunits of KLH with a molecular weight of 6-9000.000 daltons. In the hemocyanin, at least 50% of the KLH exists as a dodecamer and the remainder can be found as dodecamer aggregates. Stellar Biotechnology's KLH is purified as native molecules with high molecular weight and designated as KLH-HMW.

Formulation and Preparation: Stellar Biotechnology's KLH is provided in soluble form in a buffer solution that is composed of 10 mM sodium phosphate, 135 mM NaCl, 1 mM $CaCl_2$ and 0.5 mM $MgCl_2$. It is provided by the manufacturer in 600 mg containers at 5 mg/mL. It has re-vialed into single use vials at 2 mg/mL, 250 microliter/vial.

Stability and Storage: KLH-HMW is stable for at least 12 months when stored at 2 to 8° C.

Administration Procedures: KLH-HMW is used in vitro at a concentration of 10 mcg/mL for the generation of dendritic cells. Cells are extensively washed before administration.

TARP 27-35 (Wild Type) Peptide NSC#740703

Product Description: TARP 27-35 is a synthetic HLA-A2-restricted 9-amino acid epitope of the tumor-associated protein TARP.

Amino acid sequence: Phenylalanine-Valine-Phenylalanine-Leucine-Arginine-Asparagine-Phenylalanine-Serine-Leucine (FVFLRNFSL: SEQ ID NO: 3).

Molecular Weight: 1142.4.

Formulation and Preparation: The peptide is manufactured by NeoMPS, Inc. (San Diego, Calif.). The peptide is vialed as a 5 mL siliconized sterile amber molded glass vial containing a sterile white lyophilized powder. Each vial contains 1.1 mg of TARP 27-35 peptide and Mannitol.

Stability and Storage: The finished injectable dosage forms are stored in the freezer (−70'C) for long-term storage. Intact vials are stable for at least 6 months when stored at controlled room temperature (15° C.-30° C.) or in the refrigerator (2° C.-8° C.), and for at least 36 months when stored in the freezer (−10° C. to −25° C. and −70° C.). The peptide vial contains no preservatives; once the peptide vial is entered, unused peptide solution is discarded after 3 hours.

Administration Procedures: Autologous peptide-pulsed dendritic cell vaccines are prepared under GMP conditions from cryopreserved patient monocytes. After thaw, the monocytes are placed into a 5 day culture with rhIL-4 and rhGM-CSF to generate immature dendritic cells, followed by pulse with KLH and maturation with lipopolysaccharide (LPS) and IFN-γ. A fraction of autologous dendritic cells are pulsed separately with TARP 27-35 peptide. After removing peptide-pulsing media, individual fractions of dendritic cells are combined and concentrated down at $40\times10^6$ cells/ml in infusion media (Plasma-Lyte A containing 10% autologous heat inactivated plasma). The final peptide-loaded, volume-reduced mature dendritic cell product is prepared in sterile syringes for fresh administration intradermally.

TARP 29-37-9V Peptide (Epitope-Enhanced) NSC #740704

Product Description: TARP 29-37-9V is a synthetic HLA-A2-restricted 9-amino acid epitope of the tumor associated protein TARP, with a single amino acid substitution (valine at position 37, instead of leucine) to increase its binding affinity and immunogenicity.

Amino acid sequence: Phenylalanine-Leucine-Arginine-Asparagine-Phenylalanine-Serine-Leucine-Methionine-Valine (FLRNFSLMV; SEQ ID NO: 4).

Molecular Weight: 1126.4.

Formulation and Preparation: The peptide is manufactured by NeoMPS, Inc. (San Diego, Calif.). The peptide is vialed as a 5 mL siliconized sterile amber type 1 glass vial with a Teflon-lined stopper containing 0.5 mL of a sterile clear solution. Each mL contains 2.2 mg of TARP 29-37 (37V) Peptide and 0.5 mcL of trifluoroacetate 0.05% v/v.

Stability and Storage: The finished injectable dosage forms are stored in the freezer (−70° C.) for long-term storage. Intact vials are stable for at least 6 months when stored at controlled room temperature (15° C.-30° C.), at least 9 months when stored in the refrigerator (2° C.-8° C.), and for at least 36 months when stored in the freezer (−10° C. to −25° C. and −70° C.). The peptide vial contains no preservatives; once the peptide vial is entered, unused peptide solution is discarded after 3 hours.

Administration Procedures: Autologous peptide-pulsed dendritic cell vaccines are prepared under GMP conditions from cryopreserved patient monocytes. After thaw, the monocytes are placed into a 5 day culture with rhIL-4 and rhGM-CSF to generate immature dendritic cells, followed by pulse with KLH and maturation with LPS and IFN-γ. A fraction of autologous dendritic cells are pulsed separately with TARP 29-37-9V peptide. After removing peptide-pulsing media, individual fractions of dendritic cells are combined and concentrated down at $40\times10^6$ cells/ml in infusion media (Plasma-Lyte A containing 10% autologous heat inactivated plasma). The final peptide-loaded, volume-reduced mature dendritic cell product is prepared in sterile syringes for fresh administration intradermally.

TARP 1-20 Peptide

Amino Acid Sequence: H-Met-Gln-Met-Phe-Pro-Pro-Ser-Pro-Leu-Phe-Phe-Phe-Leu-Gln-Leu-Leu-Lys-Glyn-Ser-Ser-OH Acetate (MQMFPPSPLFFFLQLLKQSS; SEQ ID NO: 5).

Formulation and preparation: The peptide is manufactured by NeoMPS, Inc. (San Diego, Calif.). The peptide is vialed as a 2 mL clear type-1, borosilicate glass vial with a 13 mm gray, chlorobutyl, polytetrafluoroethylene (PTFE) "Teflon" lined stopper, and a 13 mm aluminum flip-off seal. Vial contains 1.2 mL of a 1 mg/mL sterile solution of TARP 1-20 Peptide (MPS-479) in dimethylsulfoxide (DMSO) with 0.1% trifluoroacetic acid (TFA).

Storage: Peptide is stored at −70° C.

Administration procedures: Autologous peptide-pulsed dendritic cell vaccines are prepared under GMP conditions from cryopreserved patient monocytes. After thaw, the monocytes are placed into a 5 day culture with rhIL-4 and rhGM-CSF to generate immature dendritic cells, followed by pulse with KLH and maturation with LPS and IFN-γ. A fraction of autologous dendritic cells is pulsed separately with TARP 1-20 peptide. After removing peptide-pulsing media, individual fractions of dendritic cells are combined and concentrated down at 40×10⁶ cells/ml in infusion media (Plasma-Lyte A containing 10% autologous heat inactivated plasma). The final peptide-loaded, volume-reduced mature dendritic cell product is prepared in sterile syringes for fresh administration intradermally.

TARP 11-30 Peptide

Amino Acid Sequence: H-Phe-Phe-Leu-Gln-Leu-Leu-Lys-Gln-Ser-Ser-Arg-Arg-Leu-Glu-His-Thr-Phe-Val-Phe-Leu-OH Acetate (FFLQLLKQSSRRLEHTFVFL; SEQ ID NO: 6).

Formulation and preparation: The peptide is manufactured by NeoMPS, Inc. (San Diego, Calif.). The peptide is vialed as a 2 mL clear type-1, borosilicate glass vial with a 13 mm gray, chlorobutyl, PTFE "Teflon" lined stopper, and a 13 mm aluminum flip-off seal. Vial contains 1.2 mL of a 1 mg/mL sterile solution of TARP 11-30 Peptide (MPS-480) in DMSO with 0.1% TFA.

Storage: Peptide is stored at −70° C.

Administration procedures: Autologous peptide-pulsed dendritic cell vaccines are prepared under GMP conditions from cryopreserved patient monocytes. After thaw, the monocytes are placed into a 5 day culture with rhIL-4 and rhGM-CSF to generate immature dendritic cells, followed by pulse with KLH and maturation with LPS and IFN-γ. A fraction of autologous dendritic cells is pulsed separately with TARP 11-30 peptide. After removing peptide-pulsing media, individual fractions of dendritic cells are combined and concentrated down at 40×10⁶ cells/ml in infusion media (Plasma-Lyte A containing 10% autologous heat inactivated plasma). The final peptide-loaded, volume-reduced mature dendritic cell product is prepared in sterile syringes for fresh administration intradermally.

TARP 21-40 Peptide

Amino Acid Sequence: H-Arg-Arg-Leu-Glu-His-Thr-Phe-Val-Phe-Leu-Arg-Asn-Phe-Ser-Leu-Met-Leu-Leu-Arg-Gly-OH Acetate (RRLEHTFVFLRNFSLMLLRG; SEQ ID NO: 7).

Formulation and preparation: The peptide is manufactured by NeoMPS, Inc. (San Diego, Calif.). The peptide is vialed as a 2 mL clear type-1, borosilicate glass vial with a 13 mm gray, chlorobutyl, PTFE "Teflon" lined stopper, and a 13 mm aluminum flip-off seal. Vial contains 1.2 mL of a 1 mg/mL sterile solution of TARP 21-40 Peptide (MPS-481) in sterile water for injection.

Storage: Peptide is stored at −70° C.

Administration procedures: Autologous peptide-pulsed dendritic cell vaccines are prepared under GMP conditions from cryopreserved patient monocytes. After thaw, the monocytes are placed into a 5 day culture with rhIL-4 and rhGM-CSF to generate immature dendritic cells, followed by pulse with KLH and maturation with LPS and IFN-γ. A fraction of autologous dendritic cells is pulsed separately with TARP 21-40 peptide. After removing peptide-pulsing media, individual fractions of dendritic cells are combined and concentrated down at 40×10⁶ cells/ml in infusion media (Plasma-Lyte A containing 10% autologous heat inactivated plasma). The final peptide-loaded, volume-reduced mature dendritic cell product is prepared in sterile syringes for fresh administration intradermally.

TARP 31-50 Peptide

Amino Acid Sequence: H-Arg-Asn-Phe-Ser-Leu-Met-Leu-Leu-Arg-Gly-Ile-Gly-Lys-Lys-Arg-Arg-Ala-Thr-Arg-Phe-OH Acetate (RNFSLMLLRGIGKKRRATRF: SEQ ID NO: 8).

Formulation and preparation: The peptide is manufactured by NeoMPS, Inc. (San Diego, Calif.). The peptide is vialed as a 2 mL clear type-1, borosilicate glass vial with a 13 mm gray, chlorobutyl, PTFE "Teflon" lined stopper, and a 13 mm aluminum flip-off seal. Vial contains 1.2 mL of a 1 mg/mL sterile solution of TARP 31-50 Peptide (MPS-482) in sterile water for injection.

Storage: Peptide is stored at −70° C.

Administration procedures: Autologous peptide-pulsed dendritic cell vaccines are prepared under GMP conditions from cryopreserved patient monocytes. After thaw, the monocytes are placed into a 5 day culture with rhIL-4 and rhGM-CSF to generate immature dendritic cells, followed by pulse with KLH and maturation with LPS and IFN-γ. A fraction of autologous dendritic cells is pulsed separately with TARP 31-50 peptide. After removing peptide-pulsing media, individual fractions of dendritic cells are combined and concentrated down at 40×10⁶ cells/ml in infusion media (Plasma-Lyte A containing 10% autologous heat inactivated plasma). The final peptide-loaded, volume-reduced mature dendritic cell product is prepared in sterile syringes for fresh administration intradermally.

TARP 41-58 Peptide

```
Amino Acid Sequence:
(IGKKRRATRFWDPRRGTP; SEQ ID NO: 9)
H-Ile-Gly-Lys-Lys-Arg-Arg-Ala-Thr-Arg- Phe-Trp-Asp-Pro-Arg-Arg-Gly-Thr-Pro- OH Acetate.
```

Formulation and preparation: The peptide is manufactured by NeoMPS, Inc. (San Diego, Calif.). The peptide is vialed as a 2 mL clear type-1, borosilicate glass vial with a 13 mm gray, chlorobutyl, PTFE "Teflon" lined stopper, and a 13 mm aluminum flip-off seal. Vial contains 1.2 mL of a 1 mg/mL sterile solution of TARP 41-58 Peptide (MPS-483) in sterile water for injection.

Storage: Peptide is stored at −70° C.

Administration procedures: Autologous peptide-pulsed dendritic cell vaccines are prepared under GMP conditions from cryopreserved patient monocytes. After thaw, the monocytes are placed into a 5 day culture with rhIL-4 and rhGM-CSF to generate immature dendritic cells, followed by pulse with KLH and maturation with LPS and IFN-γ. A fraction of autologous dendritic cells is pulsed separately with TARP 41-58 peptide. After removing peptide-pulsing media, dendritic cells, individual fractions are combined and concentrated down at 40×10⁶ cells/ml in infusion media (Plasma-Lyte A containing 10% autologous heat inactivated plasma). The final peptide-loaded, volume-reduced mature dendritic cell product is prepared in sterile syringes for fresh administration intradermally.

Detection of Anti-TARP Antibody and Cellular Responses

To determine the immunogenicity of autologous multi-epitope TARP dendritic cell vaccination, quantitative anti-TARP antibody testing is performed at Weeks 0, 12, 18, 24, 48, 72 and 96. Immunogenicity is indicated by a 3-fold increase in anti-TARP antibody concentration (measured as mcg/ml) or a 4-fold increase in antibody dilution titers over baseline.

Vaccine-induced anti-TARP and anti-PSA antibody profiles also are evaluated at Weeks 0, 12, 18, 24, 48, 72 and 96 by peptide microarray.

At weeks 0, 12, 48, 24 and 48, TARP-specific cellular responses are evaluated. CFSE proliferation, ICS, ELISPOT (IFN-γ, granzyme B, perforin) and tetramer assays are performed.

Example 2

Dendritic Cell Vaccine Preparation

ME TARP Vaccine Preparation
Autologous Cell Harvest

Blood collection is by standard lymphapheresis; 15 to 18 liters of whole blood is processed in order to collect peripheral blood mononuclear cells (MNC) with a target number of at least $2.2 \times 10^9$ monocytes. Lymphocytes are also cryopreserved. Apheresis is performed using approved standard operating procedures. Bilateral peripheral venous access is used for apheresis whenever possible. Alternatively, a temporary femoral central venous catheter (CVL) is placed as an outpatient, if indicated, for collection on the day of apheresis. Prophylactic intravenous $CaCl_2$ and $MgSO_4$ infusions may be administered during apheresis to treat or prevent citrate toxicity.

Multi Epitope TARP Peptide-Pulsed Dendritic Cells

Autologous dendritic cells prepared from peripheral blood monocytes are loaded with the following 7 different TARP-derived peptides:

```
TARP 27-35 (SEQ ID NO: 3)

TARP 29-37-9V (SEQ ID NO: 4)

TARP 1-20: (SEQ ID NO: 5)
MQMFPPSPLFFFLQLLKQSS

TARP 11-30: (SEQ ID NO: 6)
FFLQLLKQSSRRLEHTFVFL

TARP 21-40: (SEQ ID NO: 7)
RRLEHTFVFLRNFSLMLLRG

TARP 31-50: (SEQ ID NO: 8)
RNFSLMLLRGIGKKRRATRF

TARP 41-58: (SEQ ID NO: 9)
IGKKRRATRFWDPRRGTP
```

Different fractions of autologous dendritic cells are pulsed individually with only one of these peptides and the seven fractions are combined before administration to the patient.

Formulation and Preparation ME TARP DC Vaccine

Autologous peptide-pulsed dendritic cell vaccines are prepared under cGMP conditions from cryopreserved patient monocytes obtained during the original Week 0 apheresis. Autologous monocytes for dendritic cell culture are enriched from peripheral blood MNC apheresis collections by counter-flow elutriation, aliquoted into at least 8 vials with ~$333 \times 10^6$ cells/vial and cryopreserved for future preparation of the dendritic cell products. After thaw, the monocytes are placed into a 5 day culture with rhIL-4 and rhGM-CSF to generate immature dendritic cells, followed by pulse with KLH and maturation with LPS and IFN-γ, and pulsed with TARP peptide. After removing peptide-pulsing media, dendritic cells are concentrated down at $40 \times 10^6$ cells/ml in infusion media (Plasma-Lyte A containing 10% autologous heat inactivated plasma). The final peptide-loaded, volume-reduced mature dendritic cell product is prepared in sterile syringes for fresh administration intradermally.

Elutriated Monocyte Placebo Vaccine Preparation

Autologous Cell Harvest

Blood collection is by standard lymphapheresis; 10 to 15 liters of whole blood is processed in order to collect peripheral blood mononuclear cells (PBMC). Lymphocytes are also be cryopreserved. Apheresis is performed using approved standard operating procedures. Bilateral peripheral venous access is used for apheresis whenever possible. Alternatively, a temporary femoral central venous catheter (CVL) is placed as an outpatient, if indicated, for collection on the day of apheresis. Prophylactic intravenous $CaCl_2$ and $MgSO_4$ infusions may be administered during apheresis to treat or prevent citrate toxicity.

Formulation and Preparation Elutriated Monocyte Placebo Vaccine

Autologous elutriated monocyte placebo cell vaccines are prepared under cGMP conditions from cryopreserved patient PBMCs obtained during the original Week 0 apheresis and aliquoted into at least 8 vials with ~$333 \times 10^6$ cells/vial and cryopreserved for future preparation of elutriated monocyte placebo cell products. Elutriated monocytes are thawed the morning of scheduled vaccine delivery. After thaw, elutriated monocytes are concentrated down at $40 \times 10^6$ cells/ml in infusion media (Plasma-Lyte A containing 10% autologous heat inactivated plasma). The final, volume-reduced elutriated monocyte product is prepared in sterile syringes for fresh administration intradermally.

Stability and Storage

Autologous ME TARP peptide-pulsed dendritic cell vaccines are harvested from the 5-day culture product and autologous elutriated monocyte placebo vaccine from the single day thaw product. Both are packaged for fresh administration on the same day. A fixed autologous ME TARP peptide-pulsed dendritic cell or elutriated monocyte placebo vaccine dose of $20 \times 10^6$ viable cells/in 0.25 ml or 0.5 ml is administered immediately upon receipt in the clinical setting. Post packaging tests indicated that the product is stable for at least 2 hours.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A composition comprising five non-identical overlapping T cell receptor γ alternate reading frame protein (TARP) peptides, wherein the amino acid sequences of the five overlapping TARP peptides consist of SEQ ID NO: 5, SEQ ID NO: 6, SEQ ID NO: 7, SEQ ID NO: 8, and SEQ ID NO: 9.

2. The composition of claim 1, further comprising a TARP peptide consisting of SEQ ID NO: 3 and a TARP peptide consisting of SEQ ID NO: 4.

3. The composition of claim 1, further comprising a pharmaceutically acceptable carrier.

4. The composition of claim 1, further comprising an adjuvant.

5. The composition of claim 1, comprising antigen presenting cells (APCs) loaded with the TARP peptides.

6. The composition of claim 5, wherein the APCs are dendritic cells.

7. The composition of claim 1 in unit dose form.

8. The composition of claim 7, comprising a lyophilized powder of the TARP peptides.

9. A method of treating a subject having prostate cancer or breast cancer comprising selecting a subject having prostate cancer or breast cancer that expresses TARP and administering to the subject a therapeutically effective amount of the composition of claim 1, thereby treating the subject.

10. The method of claim 9, wherein the composition comprises APCs loaded with the TARP peptides.

11. The method of claim 10, wherein the APCs are dendritic cells.

12. The method of claim 10, wherein the APCs are autologous.

13. The method of claim 10, wherein the therapeutically effective amount of the composition comprises about $1 \times 10^6$ to about $30 \times 10^6$ viable APCs.

14. The method of claim 9, comprising administering the composition intradermally, intravenously, intramuscularly or subcutaneously.

* * * * *